(12) United States Patent
Birkett et al.

(10) Patent No.: US 8,245,572 B2
(45) Date of Patent: Aug. 21, 2012

(54) SYSTEM AND METHOD FOR ANALYSIS OF WELL FLUID SAMPLES

(75) Inventors: Graham Birkett, Montrouge (FR); David MacWilliam, Aberdeenshire (GB); Paul Ross, Rio de Janeiro (BR); Mangus Wardle, Kincardineshire (GB); Malcolm Atkinson, Aberdeenshire (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 369 days.

(21) Appl. No.: 12/522,557

(22) PCT Filed: Jan. 16, 2008

(86) PCT No.: PCT/EP2008/050445
§ 371 (c)(1), (2), (4) Date: Feb. 2, 2010

(87) PCT Pub. No.: WO2008/087156
PCT Pub. Date: Jul. 24, 2008

(65) Prior Publication Data
US 2010/0132449 A1    Jun. 3, 2010

(30) Foreign Application Priority Data
Jan. 17, 2007 (GB) .................. 0700835.2

(51) Int. Cl.
*E21B 49/08* (2006.01)
(52) U.S. Cl. .................................... 73/152.23
(58) Field of Classification Search ............ 73/152.23, 73/863.71–863.86
See application file for complete search history.

(56) References Cited

U.S. PATENT DOCUMENTS

| | | | | |
|---|---|---|---|---|
| 3,813,945 A * | 6/1974 | Crumal | | 73/863.02 |
| 4,147,062 A * | 4/1979 | Jaeger | | 73/863.83 |
| 4,262,533 A * | 4/1981 | Jaeger | | 73/863.11 |
| 4,269,064 A * | 5/1981 | Johnson et al. | | 73/863.82 |
| 4,475,410 A * | 10/1984 | Jaeger | | 73/863.84 |
| 4,479,393 A * | 10/1984 | Shores | | 73/863.82 |
| 4,702,114 A * | 10/1987 | Cabannes | | 73/863.85 |
| 4,744,255 A * | 5/1988 | Jaeger | | 73/863.84 |
| 4,813,270 A * | 3/1989 | Baillie | | 73/861.04 |
| 5,101,164 A * | 3/1992 | Marrelli | | 324/640 |
| 5,109,708 A * | 5/1992 | Lawless | | 73/863.11 |
| 5,134,879 A | 8/1992 | Wong et al. | | |
| 5,296,197 A * | 3/1994 | Newberg et al. | | 422/537 |
| 5,394,339 A | 2/1995 | Jones | | |
| 5,463,908 A | 11/1995 | Rosolia | | |
| 5,637,808 A * | 6/1997 | Jaeger | | 73/863.83 |
| 5,741,962 A | 4/1998 | Birchak et al. | | |

(Continued)

FOREIGN PATENT DOCUMENTS

EP     0610098     5/2000

(Continued)

*Primary Examiner* — John Fitzgerald
(74) *Attorney, Agent, or Firm* — Stephanie Chi; Matthias Abrell; Robin Nava (57) ABSTRACT

A system and method facilitates the analysis and sampling of well fluid. A sampling and data collection device is used to detect well fluid properties in situ at a flowline installation. In an exemplary embodiment, the sampling and data collection device comprises a sample collection system having a probe adapted to selectively insert into and selectively retract from the flowline to collect a fluid sample, and a sensor system to determine PVT data in situ at the location where the probe is inserted into the flowline.

24 Claims, 5 Drawing Sheets

U.S. PATENT DOCUMENTS

| | | | |
|---|---|---|---|
| RE35,824 E * | 6/1998 | Welker | 73/863.83 |
| 6,182,505 B1 * | 2/2001 | Segeral | 73/61.44 |
| 6,435,279 B1 | 8/2002 | Howe et al. | |
| 6,939,717 B2 * | 9/2005 | Jiang et al. | 436/121 |
| 7,008,793 B2 * | 3/2006 | Duriez et al. | 436/29 |
| 7,231,819 B2 * | 6/2007 | Jones et al. | 73/152.23 |
| 7,272,981 B2 * | 9/2007 | Bigalke | 73/863.85 |
| 7,314,759 B2 * | 1/2008 | Bigalke | 436/23 |
| 7,748,266 B2 * | 7/2010 | Evrard et al. | 73/152.23 |
| 8,082,780 B2 * | 12/2011 | Vannuffelen et al. | 73/152.27 |
| 2004/0045350 A1 * | 3/2004 | Jones et al. | 73/152.23 |
| 2005/0241382 A1 * | 11/2005 | Coenen | 73/152.19 |
| 2005/0279499 A1 | 12/2005 | Tarvin et al. | |

FOREIGN PATENT DOCUMENTS

| | | |
|---|---|---|
| EP | 1686238 | 8/2006 |
| GB | 2362469 | 11/2001 |
| WO | 9400671 | 1/1994 |
| WO | 0198630 | 12/2001 |

* cited by examiner

SYSTEM AND METHOD FOR ANALYSIS OF WELL FLUID SAMPLES

BACKGROUND OF THE INVENTION

1. Field of the Invention

The present invention generally relates to a system and methodology for analyzing well fluid samples. In, for example, a subsea environment, tubing is used to convey well fluid to a desired location. Samples of the fluid moving through the tubing can provide information helpful for improved operation of the well.

2. Description of Related Art

In many well applications, fluid samples are collected for analysis. For example, fluid samples may be collected for reservoir characterization. Samples are collected to deduce reservoir fluid properties, and the analysis generally is done at a land-based or field-deployed pressure/volume/temperature (PVT) laboratory. The information derived is used for periodic reservoir characterization over the life of a well to facilitate the evaluation of reserves and for production planning and optimization. Fluid samples also are collected to enable deposition studies. For example, samples may be collected to carry out wax and asphaltene deposition studies. In subsea applications, problematic deposition of such materials can occur as a result of the temperature and pressure gradients between a subsea wellhead and the surface.

In many of these same well applications, PVT data and hydrogen sulfide ($H_2S$) level data are used to facilitate optimization of well fluid production. For example, the PVT data can be used to correct volumetric correlations applied to flow meters, and the $H_2S$ level data is useful in mitigating the effects of $H_2S$ on pipelines and other downstream assets. However, the detection of the various well parameters and the taking of samples for further analysis can be difficult and/or inefficient, particularly in certain environments, such as subsea environments.

BRIEF SUMMARY OF THE INVENTION

In general, the present invention provides a system and methodology that facilitates the collection of fluid samples from a tubing, e.g. flow line, and the in-situ determination of flowline fluid properties. A sampling and data collection device is designed for coupling to a flowline at a flowline installation. The sampling and data collection device comprises a sample collection system having a probe adapted to selectively insert into, and selectively retract from, the flowline to collect a fluid sample. The sampling and data collection device also comprises a sensor system to determine PVT data in situ at the location where the probe is inserted into the flowline.

BRIEF DESCRIPTION OF THE DRAWINGS

Certain embodiments of the invention will hereafter be described with reference to the accompanying drawings, wherein like reference numerals denote like elements, and.

DETAILED DESCRIPTION OF THE INVENTION

In the following description, numerous details are set forth to provide an understanding of the present invention. However, it will be understood by those of ordinary skill in the art that the present invention may be practiced without these details and that numerous variations or modifications from the described embodiments may be possible.

The present invention generally relates to a system and methodology for the collection of fluid samples, e.g. oil, water and/or gas samples, from a flowline and the in situ determination of well fluid properties. A sampling and data collection device is used for the retrieval of fluid samples and the collection of data in situ at a flowline installation located at a well site. The device is particularly amenable to use at subsea flowline installations, such as pipeline installations, subsea wellhead installations and flow meter installations. However, the flowline installation also can be located on the surface or in other environments.

In a subsea installation, for example, the present invention makes possible the collection of desired fluid samples from a flowline, the in situ determination of PVT properties of the flowline fluids, and the in situ determination of $H_2S$ levels in the flowline fluids. The sampling and data collection device can be moved to the desired subsea installation through the use of a remotely operated vehicle (ROV) which transports the device to the sampling point and docks securely at the sampling point. A variety of ROVs are commercially available for use in transporting the device to desired subsea locations. Once docked at the installation, the ROV umbilical can be used to provide power, heat, control channels and data collection channels for the sampling and data collection device.

Figure 1:
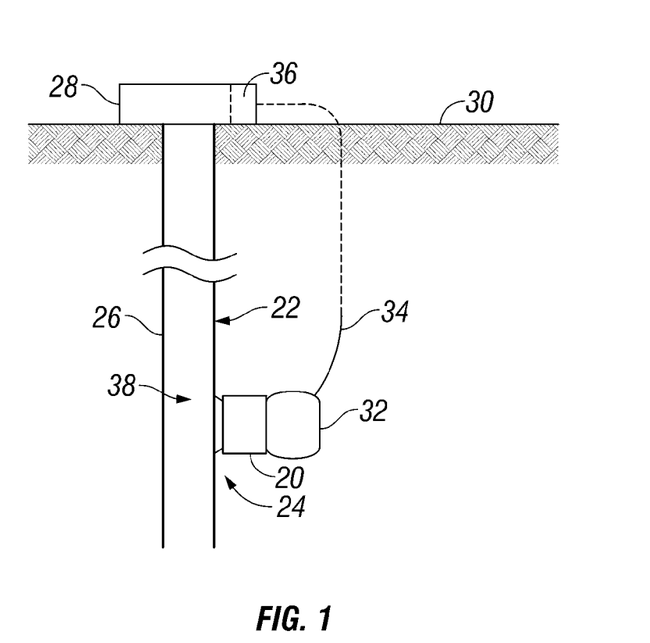
FIG. 1 is a schematic view of a system for collecting fluid samples and data on well fluid parameters, according to an embodiment of the present invention.
Figure 2:
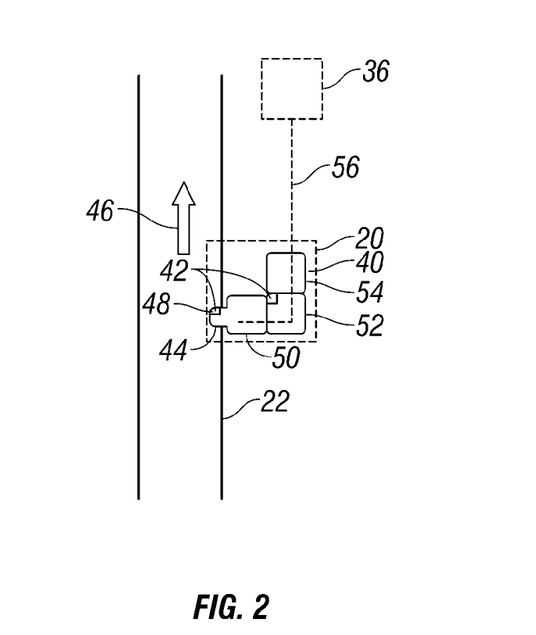
FIG. 2 is a schematic illustration of a sampling and data collection device connected at a subsea installation, according to an embodiment of the present invention.

Referring generally to FIG. 1, an embodiment of a sampling and data collection device 20 is illustrated as coupled to a flowline 22 at a flowline installation 24. In this example, flowline installation 24 comprises a tubing 26 deployed in a subsea environment. For example, the tubing 26 may extend downwardly from a surface structure 28, e.g. a platform or a ship, at a surface location 30. The sampling and data collection device 20 has been positioned at flowline installation 24 by an ROV 32 having an umbilical 34 extending to, for example, a control system 36 that may be located at the surface. The device 20 is coupled to flowline 22 for determination of flowline fluid properties and the collection of fluid samples from a specific sampling location 38.

Sampling and data collection device 20 generally comprises a sample collection system 40 and a sensor system 42 used, for example, to determine PVT properties and H$_2$S levels. The sample collection system 40 comprises a probe 44 that is selectively insertable into flowline 22 to collect one or more samples of a flowline fluid 46. The probe 44 also may comprise one or more sensors 48 that are selectively exposed to the fluids flowing through flowline 22 for in situ evaluation of flowline fluid properties, e.g. PVT properties. As discussed in greater detail below, sampling and data collection device 20 may comprise a variety of cooperating assemblies, including a probe assembly 50, an enrichment and PVT assembly 52, and a sample collection assembly 54.

Additionally, the overall sampling and data collection device 20 and each of its assemblies can be controlled by a control system, such as control system 36. Depending on the environment and specific flowline installation at which device 20 is used, control system 36 may comprise a variety of forms and may be placed at a variety of locations. For example, control system 36 may be a processor based control system, and the control system may be positioned at a surface location. Alternatively, the control system 36 can be placed proximate the sampling and data collection device 20 or at a location remote from the well site. For example, control over operation of the sampling and data collection device can be exercised remotely via an Internet link. In subsea applications, communication signals can be transmitted via umbilical 34 or over other hard-wired or wireless communication lines 56 between control system 36 and sampling and data collection device 20.

Figure 3:
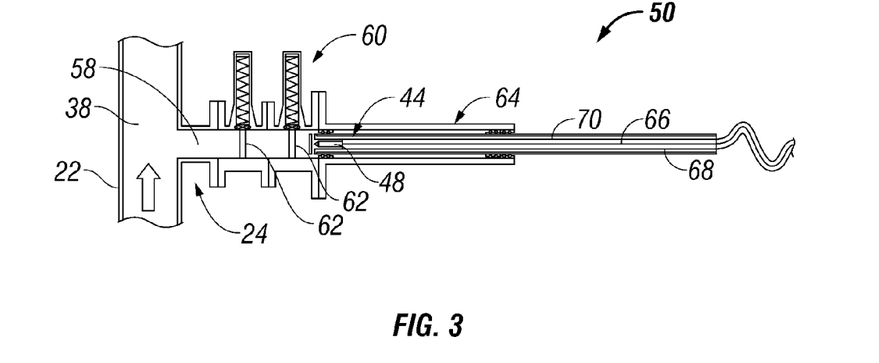
FIG. 3 is a more detailed illustration of a probe assembly that forms part of the sampling and data collection device illustrated in FIG. 2, according to an embodiment of the present invention.
Figure 4:
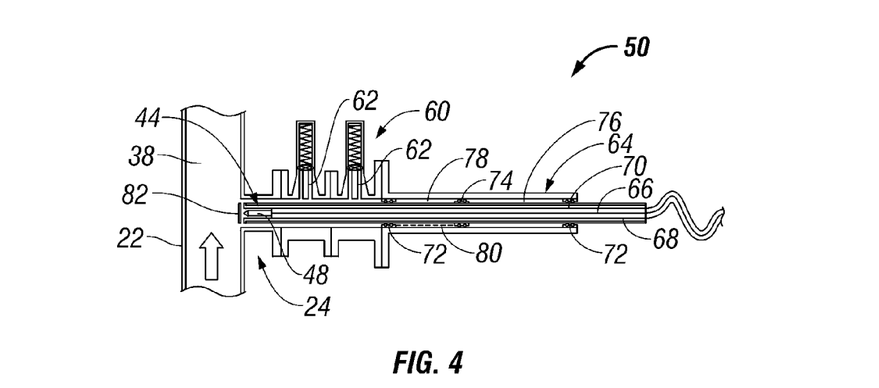
FIG. 4 is a view similar to the view illustrated in FIG. 3 but showing the probe assembly actuated to a different position, according to an embodiment of the present invention.
Figure 5:
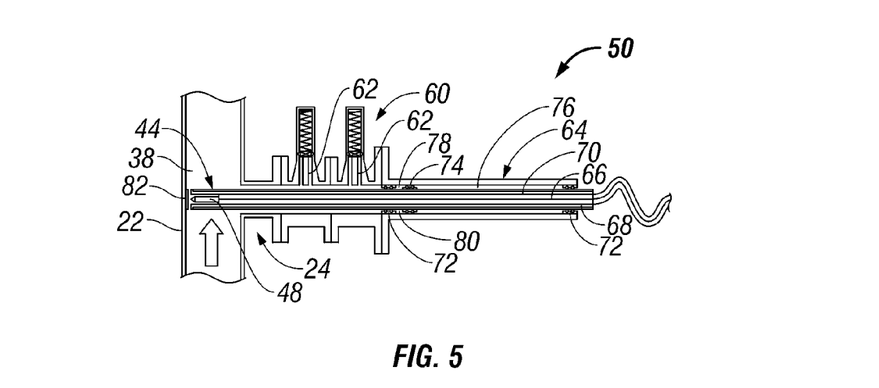
FIG. 5 is a view similar to the view illustrated in FIG. 3 but showing the probe assembly actuated to another operative position, according to an embodiment of the present invention.

Referring generally to FIGS. 3-5, an embodiment of probe assembly 50 is illustrated. As sampling and data collection device 20 is docked at flowline installation 24, probe 44 of probe assembly 50 is aligned with a corresponding opening 58 into flowline 22 to enable data collection and sampling at the desired sampling point 38. A gate valve assembly 60 may be used to control access to the flowline fluids within flowline 22 via opening 58. In the embodiment illustrated, gate valve assembly 60 comprises a plurality of gate valves 62 that are initially in a closed position, as illustrated best in FIG. 3.

Probe 44 is slidably mounted in an actuator 64 that enables selective probe insertion into the flow of fluid through flowline 22. Probe 44 also comprises the one or more sensors 48 which may be mounted proximate the probe tip for movement toward and into flowline 22. Sensor 48 can be used to detect the phase of fluid flowing past the tip of probe 44 and to detect other flowline fluid parameters, such as a flowline pressure and temperature data. Data from sensor 48 may be communicated to other parts of sampling and data collection device 20 and/or to control system 36 via a probe communication line 66. In one embodiment, sensor 48 comprises an optical sensor, and communication line 66 comprises a fiber optic line.

The probe assembly 50 also comprises a sample collection line 68 through which one or more samples of fluid flowing through flowline 22 can be drawn into sampling and data collection device 20. Additionally, an expulsion line 70 may be routed along probe 44. The expulsion line 70 accommodates the redirection of unwanted fluids, e.g. waste liquids and gases, from sampling and data collection device 20 back into flowline 22.

When the flowline fluid sampling and/or flowline fluid property determination is to be initiated, gate valves 62 are opened, as illustrated best in FIG. 4. The probe 44 is then moved through opening 58 for exposure to fluid flowing along flowline 22. The probe is moved by actuator 64 which may comprise, for example, a hydraulic actuator. In this example, probe 44 is slidably mounted in seals 72 and is moved by pressure acting on a piston member 74 coupled to probe 44 and located between seals 72. As with conventional hydraulic actuators, a hydraulic fluid can be introduced into a chamber 76 on one side of piston member 74 to move probe 44 towards flowline 22. The probe 44 can be adjusted in an opposed direction by introducing hydraulic fluid into a chamber 78 on an opposite side of piston member 74. Additionally, actuator 64 may comprise a spring number 80 positioned to automatically retract probe 44 to an outlying position beyond gate valves 62 in the event of an unexpected power failure.

Once gate valve assembly 60 is opened, probe 44 can be traversed in either direction across the interior of flowline 22 to assess variations in phase present at different positions across the flowline. For example, probe 44 can be traversed between a minimally invasive position, as illustrated in FIG. 4, and a fully extended position at an opposed side of the flowline from opening 58, as illustrated in FIG. 5. During this traversing process, phase, pressure and temperature data are obtained with sensor 48. Based on an assessment of this data, probe 44 can be traversed to an optimum position to obtain a sample for enrichment. For example, if a liquid sample is to be captured first, then probe 44 is traversed to a position within the flowline where the most liquid was detected during the traversing process. Actuator 64 also can be designed to rotate probe 44 into or away from the flow direction of the flowline fluid to further optimize the selective sampling and/or sensing of gas and/or liquid flowing through flowline 22. For example, if the gas sample is to be captured, probe 44 can be rotated until its sampling port 82 is directed downstream. This orientation enhances gas collection rates in a mixed flow.

Upon withdrawing a sample from flowline 22, the sample is directed to enrichment and PVT assembly 52 for further in situ evaluation. In the embodiment illustrated in FIG. 6, assembly 52 comprises three chambers, referred to as an active sampling device chamber 84, a flash chamber 86, and a gas expansion chamber 88. Each of these chambers utilizes an actuator assembly 90, 92, 94, respectively. The actuator assemblies may comprise hydraulic actuator assemblies having pistons 91, 93 and 95 that can be moved to adjust the volume of each chamber in a controlled manner.

Figure 6:
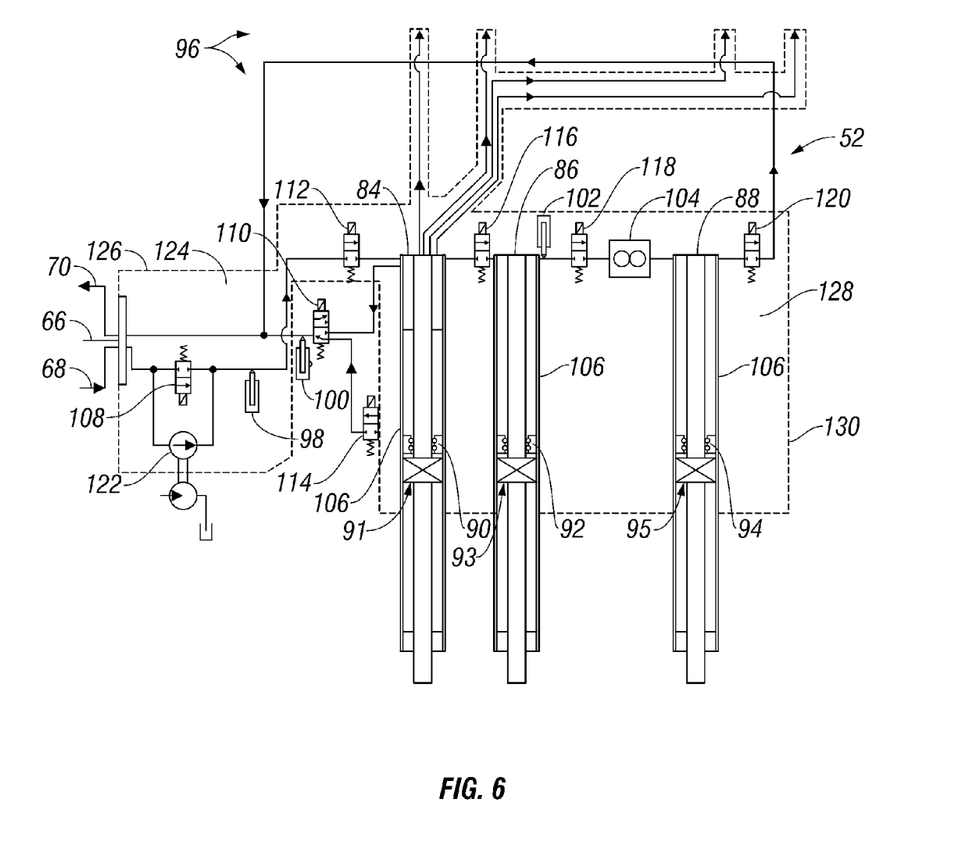
FIG. 6 is a more detailed illustration of an enrichment and PVT assembly that forms part of the sampling and data collection device illustrated in FIG. 2, according to an embodiment of the present invention.

The enrichment and PVT assembly 52 further comprises a flow network 96 coupled to sample line 68 and waste expulsion line 70 for directing fluid to and from chambers 84, 86 and 88. A variety of sensors also may be connected along flow network 96 to further sense parameters of the fluids flowing therethrough. For example, an H$_2$S sensor 98 may be coupled to sample line 68 within assembly 52. Additionally, optical sensors, such as optical sensors 100 and 102, may be coupled into flow network 96 at desired positions to provide data on the specific phase flowing along these locations at a given point in time. Another example of a sensor that may be utilized within assembly 52 is a coriolis mass flow meter 104 that enables the measurement of density and mass flow rates through specific sections of flow network 96. For example, the mass flow meter 104 may be positioned in a portion of flow network 96 connecting flash chamber 86 with gas expansion chamber 88. Other sensors 106 can be positioned in each of the chambers 84, 86 and 88 to provide pressure and temperature data for each chamber. The other sensors also may comprise density and viscosity sensors to determine densities and viscosities of the fluid during the PVT analysis. The data collected from the various sensors can be output to control system 36 for evaluation and to enable the controlled operation of enrichment and PVT assembly 52 and sample collection assembly 54.

Within assembly 52, a plurality of valves, such as valves 108, 110, 112, 114, 116, 118 and 120, may be positioned along flow network 96 to enable control of fluid flow. For example, the valves can be positioned to control the flow of fluid entering assembly 52 via sample line 68, exiting assembly 52 via waste line 70, flowing between chambers 84, 86 and 88, flowing to sample collection assembly 54, and to other components, as desired when carrying out enrichment and PVT related processes. The valves can be controlled by an operator via control system 36 which enables the operator to route fluids, e.g. liquids and gases, and to isolate fluids in a variety of ways depending on the specific analytical process undertaken by the operator. In some embodiments, control system 36 can be programmed to exercise automatic control of the valves in specific situations.

In the illustrated embodiment, assembly 52 further comprises a circulation pump 122. The circulation pump 122 can be used to assist in flushing flow network 96 and assembly 52 and to aid in heat transfer through the system by pumping well fluid or other fluid through the system. During a flushing procedure, for example, valve 108 can be moved to a closed position, and other valves throughout assembly 52 can be opened or closed, as necessary, to direct the flushing fluid through desired regions of the overall assembly. In one example, circulation pump 122 is turned on, and valves 112, 116, 118 and 120 are actuated to an open position. This causes circulation of flowline fluids through the heads of chambers 84, 86 and 88 and back to the flowline 22. This circulation of flushing fluid is useful for at least two reasons. First, the circulating fluid helps flush dead fluids from the sampling lines and other parts of assembly 52. Secondly, the flushing fluid transfers heat energy from the flowline fluids to the sampling system which helps increase the temperature of a designated "line condition zone" to flowline conditions.

Additionally, temperature control systems can be incorporated into enrichment and PVT assembly 52 to control the heating and/or cooling of specific regions of the assembly. For example, a temperature control system 124 can be used to vary temperature within a region 126 located generally where sample line 68 enters assembly 52. The temperature control system 124 may comprise a temperature maintenance jacket deployed about the specific components illustrated. A second temperature control system 128 can be used to, for example, maintain a second region 130 generally surrounding chambers 84, 86 and 88 at a standard temperature. The second temperature control system also may comprise a temperature maintenance jacket deployed about the specific components within region 130.

Figure 7:
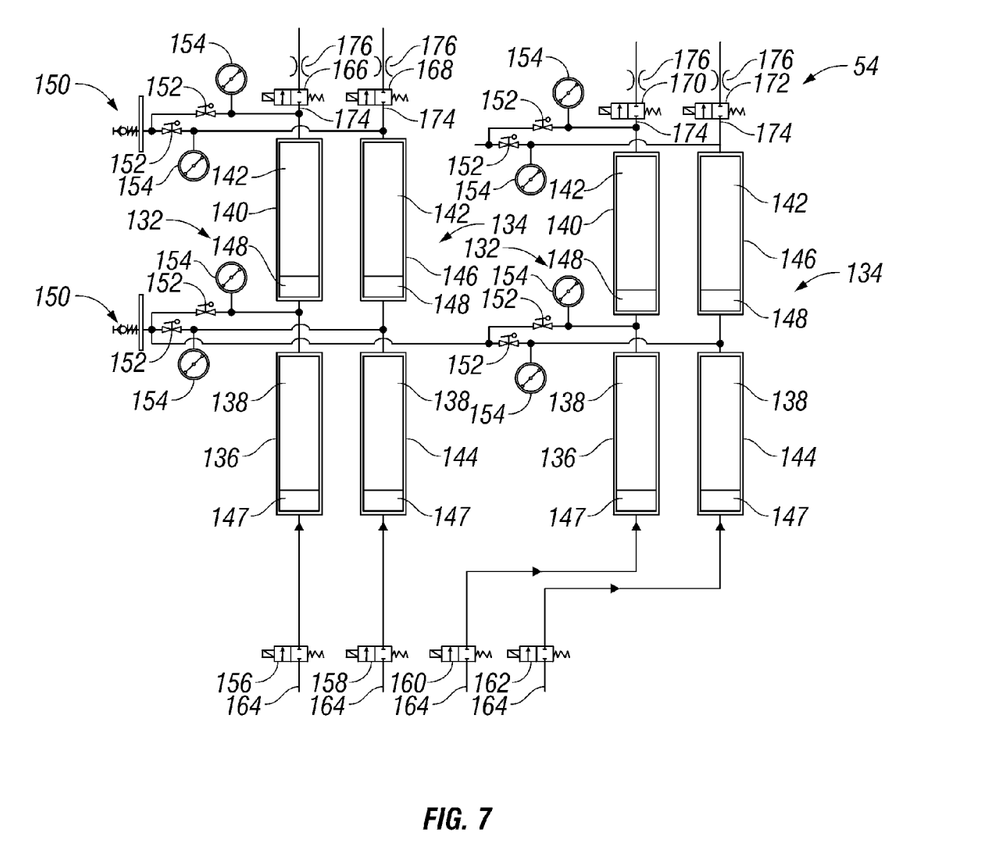
FIG. 7 is a more detailed illustration of a sample collection assembly that forms part of the sampling and data collection device illustrated in FIG. 2, according to an embodiment of the present invention.

Referring generally to FIG. 7, an example of sample collection assembly 54 is illustrated. In this embodiment, the sample collection assembly comprises a plurality of sample bottle sets including two liquid, e.g. oil, sample sets 132 and two gas sample sets 134. With this design, two gas samples and two oil samples may be retrieved in one sampling operation. However, additional sets of bottles can be added to the design to increase the number of samples that can be recovered in one deployment of the sampling system to the desired sampling location. Each liquid sample set 132 comprises a sample bottle 136, filled with buffer fluid 138, and a waste bottle 140 filled with a displaceable fluid 142, such as water glycol. Similarly, each gas sample set 134 comprises a sample bottle 144, filled with buffer fluid 138, and a waste bottle 146 filled with fluid 142.

As a sample is directed into a sample bottle 136, 144, a piston 147 is moved to displace buffer fluid 138 into the corresponding waste bottle 140, 146. The displaced buffer fluid moves a waste bottle piston 148 which simultaneously displaces the water glycol fluid 142 out of the waste bottle. In subsea applications, the water glycol fluid 142 can be displaced to the surrounding ocean.

The sample collection assembly 54 also may comprise precharge ports 150 that allow a precharge pressure to be applied to the water glycol fluid 142 and to the buffer fluid 138 while the system is being prepared for deployment to the desired sampling location. A plurality of valves 152, such as manually operable valves, can be deployed between precharge ports 150 and corresponding sample bottles 136, 144 and waste bottles 140, 146 to enable control over the application of precharge pressure. Additionally, precharge pressure gauges 154 can be used to monitor the pressure in the sample bottles and the waste bottles during precharging and after the precharging equipment is disconnected from precharge ports 150.

A plurality of controllable valves 156, 158, 160 and 162 are deployed in each sample supply line 164 used to direct a flowline fluid sample into a corresponding sample bottle 136, 144. Similarly, controllable valves 166, 168, 170 and 172 are deployed in each fluid dump line 174 through which displaceable fluid 142 is dumped to an external location. The valves enable selective and independent isolation of each sample bottle before and after taking a flowline fluid sample. Additionally, flow restrictors 176 may be coupled to dump lines 174 to restrain the flow rate at which the flowline fluid sample enters a given sample bottle 136, 144. The flow restrictors 176 prevent unwanted pressure fluctuations during the sampling procedure.

It should be noted that control system 36 can be used both in the collection and processing of data received from sampling and data collection device 20 and to control the operation of sampling and data collection device 20. For example, control system 36 can be used to control the hydraulic signals used to stroke the actuators of the probe assembly 50 and enrichment and PVT assembly 52. The control system can be used to control the circulation pump 122 and to control the various valves positioned throughout enrichment and PVT assembly 52 and sample collection assembly 54. In one embodiment, the valves used are solenoid control valves, and the electrical signals provided to operate the solenoid control valves are controlled via control system 36. The control system also can be used to maintain desired temperatures via temperature control systems 124 and 128. Additionally, data collected from, for example, the various pressure and temperature sensors, optical sensors, encoders, Coriolis meter and $H_2S$ sensor can be collected and processed by control system 36. With a processor based control system, the control system is readily programmed to interpret data from the sensors and to output appropriate control signals to the appropriate pumps, valves, temperature control systems, etc. to automate at least portions of the sampling and data collection processes performed by sampling and data collection device 20.

Figure 8:
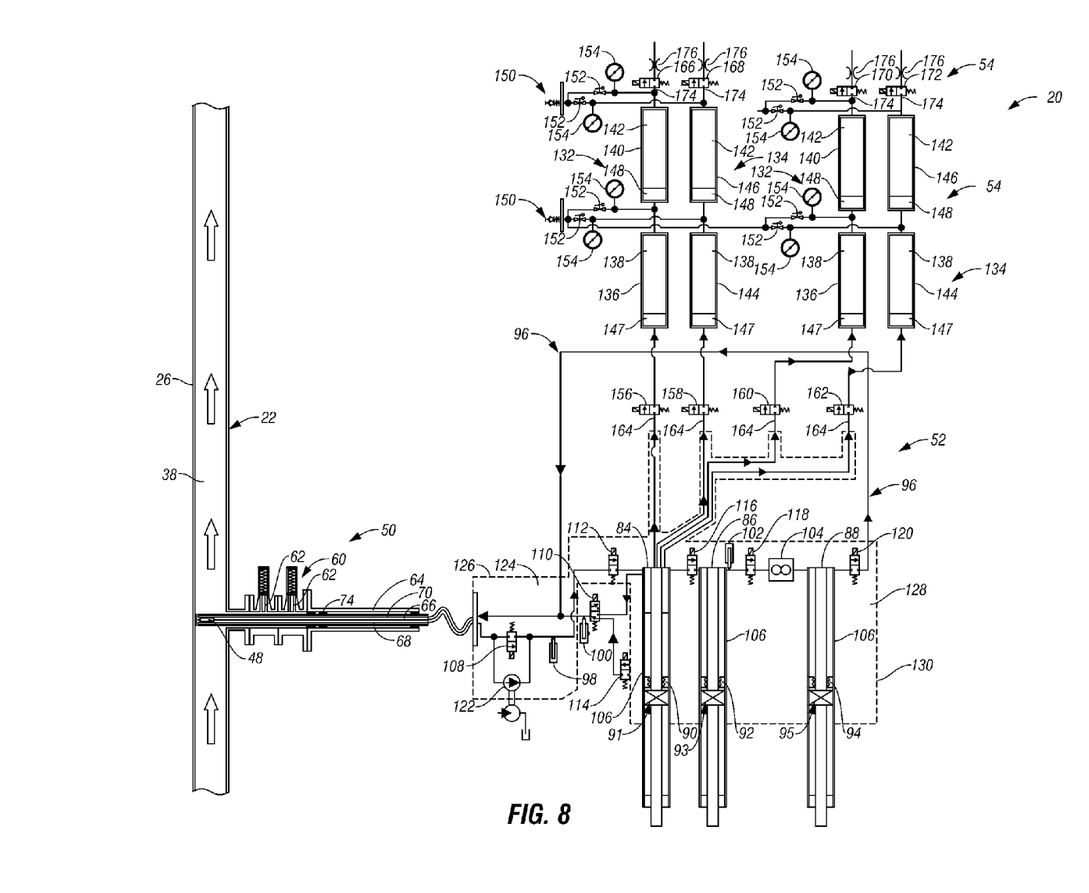
FIG. 8 is a more detailed illustration of an embodiment of the overall sampling and data collection device illustrated in FIG. 2, according to an embodiment of the present invention.

Referring generally to FIG. 8, the overall sampling and data collection device is illustrated in greater detail while docked at a flowline installation proximate a desired sampling location. With reference to FIG. 8 and the individual assembly figures discussed above, a better explanation can be provided of in situ processes that can be conducted with sampling and data collection device 20.

For example, enrichment of a flowline fluid sample can be accomplished by energizing valve 112 to an open position and drawing back piston 91 of active sampling device chamber 84 to full stroke. The valve 112 is then moved to a closed position, and the phases within the chamber are allowed to separate via gravity. Subsequently, either valve 110 or valve 114 is actuated to an open position depending on whether a gas or liquid is to be expelled. The active sampling device piston 91 is then moved forward, and the phase being expelled is monitored by optical sensor 100. Once a phase change is detected by the optical sensor 100, piston 91 is stopped to prevent further expulsion of fluid. The valve previously opened to enable the expulsion of fluid can then be closed, and, if necessary, the steps can be repeated until a sufficient volume of the desired single phase sample has been collected.

Following the enrichment process, a flowline fluid sample can be captured in sample collection assembly 54. To capture a liquid sample, for example, valves 156 and 166 are actuated to an open position. Piston 91 of active sampling device chamber 84 is then stroked forward to push the single phase enriched liquid sample into the corresponding sample bottle 136. This, in turn, discharges buffer fluid 138 into the corresponding waste bottle 140 causing fluid 142 to be discharged through valve 166. The valves 156 and 166 are then closed to isolate the sample within sample bottle 136. To capture a gas sample, the same process is followed for one of the gas sample collection bottles 144. For example, valves 158 and 168 can be actuated to an open position as the gas sample is forced into the sample bottle 144. Valves 158 and 168 are then closed to capture the gas sample. Additional liquid and gas samples can be captured by repeating the same process with valve pairs 160, 170 and 162, 172.

Sampling and data collection device 20 also can be used to take PVT measurements in situ independently of whether samples are being captured during a given operation. Such measurements often require detection and/or derivation of properties such as density, pressure, temperature, volume and phase of the fluid in various parts of the process. By way of example, density can be measured using the coriolis meter 104 positioned between flash chamber 86 and the gas expansion chamber 88. The volume of fluid enclosed in each of the chambers can be determined from piston position provided by, for example, encoders in each chamber actuator. Also, volume passing through the meter 104 can be derived from the mass flow rate and density being recorded by meter 104. Additionally, the appropriate sensors described above can be used to obtain pressure, temperature and phase data gathered at various locations within the system.

In one process example, oil PVT properties are obtained in situ. In this process, valve 116 is actuated to an open position, and piston 91 of active sampling device chamber 84 is extended while piston 93 of flash chamber 86 is retracted. The action of pistons 91 and 93 causes a subsample to be transferred isobarically from the active sampling device chamber 84 to the flash chamber 86. Valve 116 is then closed, and the flash chamber temperature is stabilized at a standard temperature, such as 60° F. (15.6° C.). The flash chamber is then expanded by retracting flash chamber piston 93 to maximum stroke or until standard pressure has been reached.

If the subsample is at standard pressure following expansion of the flash chamber 86, valve 118 is opened. The flash chamber piston 93 is extended while the gas expansion chamber piston 95 is simultaneously retracted to transfer gas through the Coriolis meter 104 to the gas expansion chamber 88 while maintaining standard pressure. The transfer of the subsample is stopped as soon as oil is detected at the flash line optical sensor 102. At this stage, the total gas volume, gas density and total oil volume at standard conditions are known and recorded for the subsample. Subsequently, piston 93 can be further extended while piston 95 is retracted to move oil through coriolis meter 104 so that oil density can be recorded at standard conditions as it passes through meter 104.

If, however, the subsample is still above standard pressure following expansion of the flash chamber 86, valve 118 is opened and only the gas expansion chamber piston 95 is retracted until standard pressure is reached. Subsequently, the flash chamber piston 93 is extended and the gas expansion chamber piston 95 is retracted simultaneously to transfer gas through the coriolis meter 104 to the gas expansion chamber 88 while maintaining standard pressure. The transfer is stopped as soon as oil is detected at flash line optical sensor 102. At this stage, the total gas volume, gas density and total oil volume at standard conditions are known and recorded for the subsample. Piston 93 then can be further extended while piston 95 is retracted to move oil through coriolis meter 104 so that oil density can be recorded at standard conditions as it passes through meter 104.

While extending the flash chamber piston 93 and retracting the gas expansion piston 95 simultaneously, the gas expansion chamber piston 95 can run out of stroke, i.e. reach its limit of travel. In this event, a gas expulsion is performed in which valve 118 is closed and valve 120 is opened. The gas expansion chamber piston 95 is then extended to transfer gas back to flowline 22. Valve 120 is then closed, and gas expansion chamber piston 95 is retracted to reduce the pressure in the gas expansion chamber to standard pressure. Valve 118 is then opened and the process continued as set forth in the preceding paragraph. The same type of gas expulsion process can be carried out if pressure is still above standard pressure after having retracted both the flash chamber piston 93 and expansion chamber piston 95.

The same processes as those described above with respect to obtaining oil PVT properties in situ can be used to measure PVT properties of a gas sample once the single phase gas sample has been enriched. However, a larger subsample of gas may be required if a density measurement is desired for condensate fluid.

Sampling and data collection device 20 can be used in a variety of applications for conducting many types of sampling and in situ fluid property analyses. The processes described above are provided as examples of processes that can be carried out by device 20 and should not be construed as limiting. Other examples of in situ processes at a flowline installation, subsea or otherwise, include recombination of gas and liquid. Gas and liquid can be recombined in correct proportions at line conditions by precisely controlling the actuators, e.g. via rotary encoders, to transfer correct proportions of gas and liquid into a PVT chamber. The pressure in the chamber can be increased by a piston actuator, such as those described above, back to reservoir pressure. The temperature also can be increased to reservoir temperature by one of the temperature control systems to provide a representative sample of fluid at reservoir conditions for further analysis. Furthermore, the piston actuator for the PVT chamber can be combined with a linear or rotary encoder configured to read directly the volume in the PVT chamber. With this information, a P-V relationship or constant mass study can be performed to determine the compressibility of a gas or oil fluid as well as a bubble point pressure of an oil fluid.

In still other processes, the PVT chamber can be provided with an optic sensor able to differentiate between gas and liquid to enable the determination of reservoir fluid type at reservoir pressure and temperature. Such an optic sensor can be used during a constant mass study as a secondary means to determine the bubble point pressure of oil. Alternatively, the optic sensor can be used as the primary means to determine dew point pressure of a gas. The PVT chamber also can be fitted with density and viscosity sensors to detect such parameters for use during, for example, a constant mass study. Other types of processes also can be employed to determine fluid composition and to predict further PVT analyses, e.g. differential vaporization, depletion studies and/or separation tests. Processes also can be carried out on device 20 to determine wax appearance temperatures on the reservoir fluid via, for example, cross polar microscopy, and asphaltene precipitation via, for example, monitoring NIR transmittance through the flowline fluid sample. In some applications, the separated liquid phase can be analyzed to determine its pH value.

Accordingly, although only a few embodiments of the present invention have been described in detail above, those of ordinary skill in the art will readily appreciate that many modifications are possible without materially departing from the teachings of this invention. Accordingly, such modifications are intended to be included within the scope of this invention as defined in the claims.

What is claimed is:

1. A subsea system for collecting fluid samples and data, comprising:
    a sampling and data collection device adapted to be coupled to a flowline at a flowline installation, the sampling and data collection device comprising:
    a sample collection system having a probe adapted to selectively insert into and selectively retract from the flowline to collect a fluid sample; and
    a sensor system to determine pressure/volume/temperature (PVT) data in situ at the location of the flowline installation where the probe is inserted into the flowline.

2. The system as recited in claim 1, wherein the sensor system comprises a phase sensor.

3. The system as recited in claim 1, wherein the sensor system comprises a temperature sensor and a pressure sensor.

4. The system as recited in claim 1, wherein the sample collection system comprises a plurality of sample collection bottles.

5. The system as recited in claim 1, wherein the sample collection system comprises at least one gas sample collection bottle and at least one liquid sample collection bottle.

6. The system as recited in claim 1, wherein the sensor system comprises a hydrogen sulfide (H2S) sensor.

7. A method of collecting information on fluids in a fluid flowline at a subsea location, comprising:
    engaging a sampling and data collection device with a flowline at a desired flowline location wherein the sampling and data collection device is capable of selectively inserting a probe into and selectively retracting the probe from the flowline;
    determining PVT properties of a flowline fluid in situ at the desired flowline location via the sampling and data collection device; and
    obtaining a flowline fluid sample at the desired flowline location via the sampling and data collection device.

8. The method as recited in claim 7, further comprising sensing H2S levels of the flowline fluid in situ at the desired flowline location via the sampling and data collection device.

9. The method as recited in claim 7, wherein engaging comprises adjustably inserting a probe into the flowline at a desired position within the flowline.

10. The method as recited in claim 7, further comprising measuring a fluid sample density and a mass flow rate with a mass flowmeter.

11. The method as recited in claim 7, wherein determining comprises determining PVT properties via a sensor mounted to a probe inserted into the flowline.

12. The method as recited in claim 7, wherein determining comprises standardizing the fluid sample pressure and temperature in an adjustable chamber and measuring PVT properties in the adjustable chamber.

13. The method as recited in claim 7, wherein obtaining comprises capturing a liquid sample in a sample bottle.

14. The method as recited in claim 7, wherein obtaining comprises capturing a gas sample in a sample bottle.

15. The method as recited in claim 7, further comprising drawing the flowline fluid into an enrichment and PVT assembly via a chamber and a chamber actuator controlled to adjust a chamber volume.

16. The method as recited in claim 15, further comprising controlling the temperature in a desired region of the enrichment and PVT assembly.

17. The method as recited in claim 15, further comprising flushing flowline fluid through the enrichment and PVT assembly prior to collecting flowline fluid data.

18. A system for collecting fluid samples and data, comprising:
    a subsea sampling and data collection device coupleable to a subsea flowline, the subsea sampling and data collection device comprising:
    a probe assembly selectively extendable into contact with a flowline fluid within the flowline;
    an enrichment and PVT assembly to enrich a flowline fluid and to determine PVT properties of the flowline fluid in situ; and
    a sample collection assembly to collect a sample of flowline fluid for subsequent analysis.

19. The system as recited in claim 18, further comprising a control system to control operation of the probe assembly, the enrichment and PVT assembly, and the sample collection assembly.

20. A method, comprising:
    moving a sampling and data collection device to a subsea location proximate a flowline;
    inserting a probe of the sampling and data collection device into the flowline for exposure to a fluid flowing in the flowline;
    determining a property of the fluid in situ; and
    withdrawing a sample of the fluid from the flowline for further analysis.

21. The method as recited in claim 20, wherein withdrawing comprises withdrawing the sample into an enrichment and PVT assembly via a plurality of chambers and chamber actuators controllable to adjust the volume of each chamber.

22. The method as recited in claim 20, further comprising changing the temperature of the sample in the sampling and data collection device.

23. The method as recited in claim 20, wherein determining comprises sensing H2S levels of the flowline fluid in situ at the desired flowline location via the sampling and data collection device.

24. The method as recited in claim 20, wherein withdrawing comprises selectively withdrawing a liquid sample and a gas sample.

* * * * *